United States Patent
Rosenberg et al.

(10) Patent No.: US 10,980,610 B2
(45) Date of Patent: Apr. 20, 2021

(54) SYSTEMS, METHODS, AND COMPUTER-READABLE STORAGE MEDIA FOR CONTROLLING ASPECTS OF A ROBOTIC SURGICAL DEVICE AND VIEWER ADAPTIVE STEREOSCOPIC DISPLAY

(71) Applicant: Covidien LP, Mansfield, MA (US)

(72) Inventors: Meir Rosenberg, Newton, MA (US); Dwight Meglan, Westwood, MA (US); William Peine, Ashland, MA (US); Albert Dvornik, Somerville, MA (US)

(73) Assignee: Covidien LP, Mansfield, MA (US)

(*) Notice: Subject to any disclaimer, the term of this patent is extended or adjusted under 35 U.S.C. 154(b) by 0 days.

(21) Appl. No.: 16/306,685

(22) PCT Filed: May 26, 2017

(86) PCT No.: PCT/US2017/034619
§ 371 (c)(1),
(2) Date: Dec. 3, 2018

(87) PCT Pub. No.: WO2017/210101
PCT Pub. Date: Dec. 7, 2017

(65) Prior Publication Data
US 2019/0298481 A1    Oct. 3, 2019

Related U.S. Application Data

(60) Provisional application No. 62/345,522, filed on Jun. 3, 2016.

(51) Int. Cl.
*A61B 90/00* (2016.01)
*A61B 34/32* (2016.01)
(Continued)

(52) U.S. Cl.
CPC .............. *A61B 90/37* (2016.02); *A61B 34/00* (2016.02); *A61B 34/30* (2016.02); *A61B 34/32* (2016.02);
(Continued)

(58) Field of Classification Search
CPC ......... A61B 90/37; A61B 34/32; A61B 34/76; G06T 7/70; G06T 7/0012; H04N 13/204;
(Continued)

(56) References Cited

U.S. PATENT DOCUMENTS 8,704,879 B1    4/2014   Cheng et al.
2006/0100642 A1  5/2006  Yang et al.
(Continued)

FOREIGN PATENT DOCUMENTS

WO    2015143067 A1    9/2015

OTHER PUBLICATIONS

International Search Report dated Sep. 7, 2017, corresponding to International Application No. PCT/US2017/034619; 2 pages.
(Continued)

*Primary Examiner* — Jamie J Atala
*Assistant Examiner* — Hesham K Abouzahra

(57) ABSTRACT

Systems, methods, and computer-readable media are provided for robotic surgical device control. A system is provided including a robotic arm, an autosteroscopic display, a user image capture device, an image processor, and a controller. The robotic arm is coupled to a patient image capture device. The autostereoscopic display is configured to display an image of a surgical site obtained from the patient image capture device. The image processor configured to identify a location of at least part of a user in an image obtained from the user image capture device. The controller is configured to, in a first mode, adjust a three dimensional aspect of the image displayed on autostereo-
(Continued)

scopic display based on the identified location, and, in a second mode, move the robotic arm or instrument based on a relationship between the identified location and the surgical site image.

16 Claims, 10 Drawing Sheets

(51) Int. Cl.
| | |
|---|---|
| A61B 34/00 | (2016.01) |
| G06T 7/70 | (2017.01) |
| H04N 13/204 | (2018.01) |
| H04N 13/305 | (2018.01) |
| H04N 13/383 | (2018.01) |
| H04N 13/398 | (2018.01) |
| G06F 3/01 | (2006.01) |
| G06T 7/00 | (2017.01) |
| H04N 5/77 | (2006.01) |
| H04N 9/82 | (2006.01) |
| A61B 34/30 | (2016.01) |

(52) U.S. Cl.
CPC ............. *A61B 34/76* (2016.02); *A61B 90/00* (2016.02); *G06F 3/013* (2013.01); *G06T 7/0012* (2013.01); *G06T 7/70* (2017.01); *H04N 5/77* (2013.01); *H04N 9/8205* (2013.01); *H04N 13/204* (2018.05); *H04N 13/305* (2018.05); *H04N 13/383* (2018.05); *H04N 13/398* (2018.05); *A61B 2034/301* (2016.02); *A61B 2090/364* (2016.02); *A61B 2090/367* (2016.02); *A61B 2090/368* (2016.02); *A61B 2090/372* (2016.02); *A61B 2090/373* (2016.02); *G06T 2207/10068* (2013.01); *G06T 2207/30196* (2013.01); *G06T 2207/30244* (2013.01)

(58) Field of Classification Search
CPC .. H04N 13/305; H04N 13/383; H04N 13/398; G06F 3/013
See application file for complete search history.

(56) References Cited

U.S. PATENT DOCUMENTS

| | | | | |
|---|---|---|---|---|
| 2008/0068372 | A1* | 3/2008 | Krah | H04N 13/302 345/419 |
| 2009/0245600 | A1* | 10/2009 | Hoffman | A61B 90/37 382/128 |
| 2010/0086199 | A1* | 4/2010 | Kim | H04N 13/275 382/154 |
| 2010/0321482 | A1* | 12/2010 | Cleveland | H04N 13/383 348/78 |
| 2012/0208564 | A1 | 8/2012 | Clark et al. | |
| 2013/0030571 | A1 | 1/2013 | Ruiz Morales et al. | |
| 2013/0317352 | A1 | 11/2013 | Case et al. | |
| 2014/0024889 | A1 | 1/2014 | Xiaoli | |
| 2014/0313190 | A1 | 10/2014 | Vesely et al. | |
| 2016/0009411 | A1* | 1/2016 | Davalos | G06F 3/012 345/156 |
| 2016/0037998 | A1* | 2/2016 | Kawashima | A61B 1/00006 600/102 |
| 2017/0172675 | A1* | 6/2017 | Jarc | A61B 1/00193 |

OTHER PUBLICATIONS

European Search Report dated Jan. 15, 2020, corresponding to counterpart European Application No. 17807282.3; 14 pages.
Chinese Office Action dated Feb. 20, 2021, issued in corresponding Chinese Appln. No. 201780032023, 14 pages.

* cited by examiner

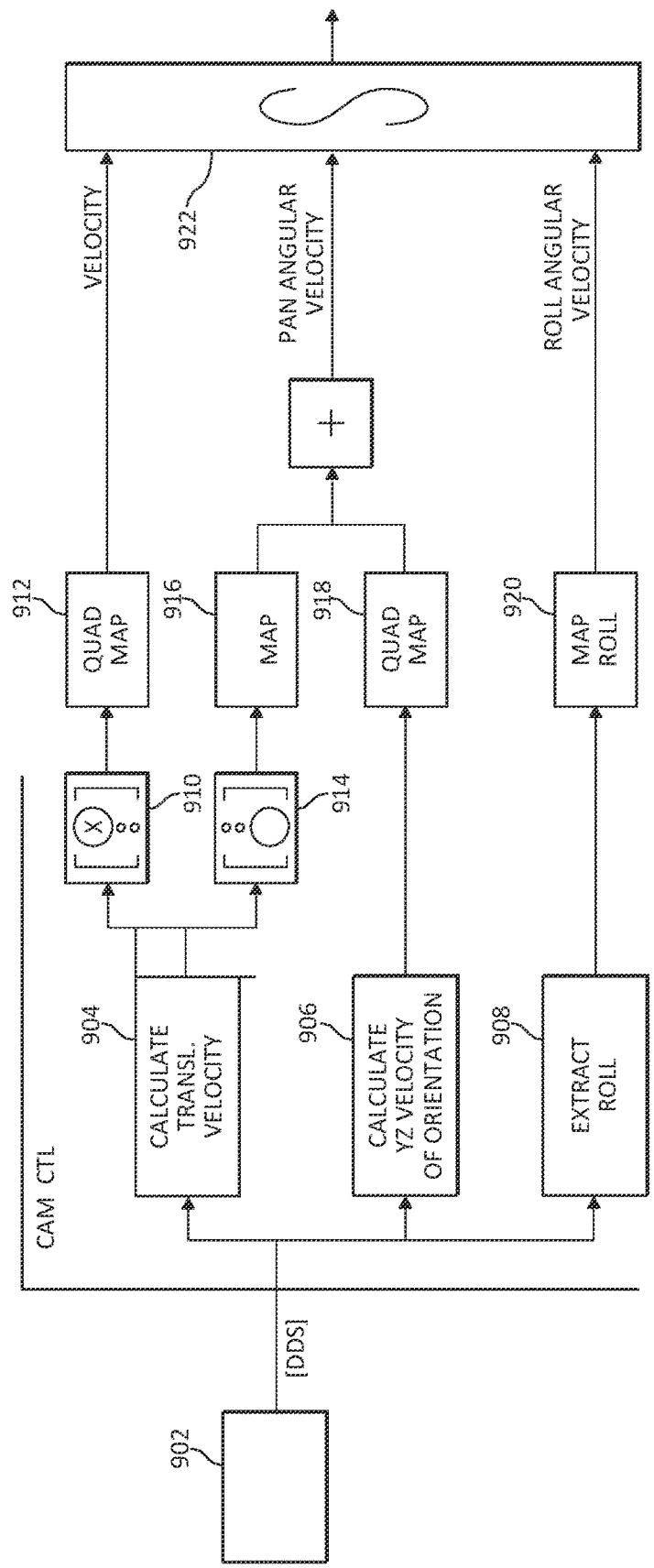
FIG. 9
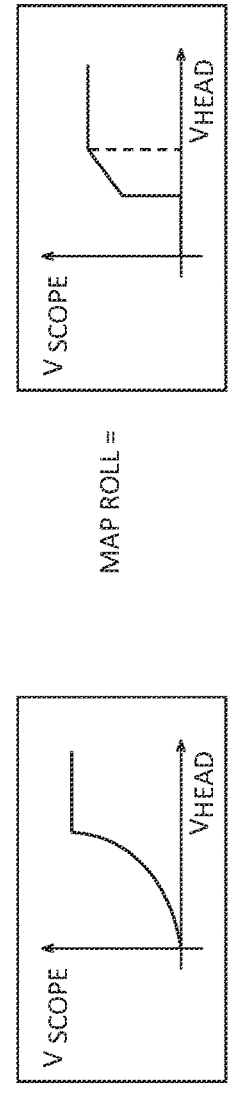
FIG. 10A
FIG. 10B

SYSTEMS, METHODS, AND COMPUTER-READABLE STORAGE MEDIA FOR CONTROLLING ASPECTS OF A ROBOTIC SURGICAL DEVICE AND VIEWER ADAPTIVE STEREOSCOPIC DISPLAY

CROSS-REFERENCE TO RELATED APPLICATIONS

This application is a U.S. National Stage Application filed under 35 U.S.C. 371(a) of International Patent Application Serial No. PCT/US2017/034619, filed May 26, 2017, which claims the benefit of and priority to U.S. Provisional Patent Application Ser. No. 62/345,522, filed Jun. 3, 2016, the entire disclosure of which is incorporated by reference herein.

BACKGROUND

Robotic surgical systems are increasingly being used in minimally invasive medical procedures. Typically, robotic surgical systems include a surgeon console located remote from one or more robotic arms to which surgical instruments and/or cameras are coupled. The surgeon console may be located on another side of the operating room from the robotic arms, in another room, or in another building, and includes input handles or other input devices for receiving inputs from a surgeon. The inputs are communicated to a central controller, which translates the inputs into commands for manipulating the robotic arms in the vicinity of a patient, for example, within a surgical site.

The surgeon console may include a stereoscopic display, sometimes referred to as a three-dimensional (3D) display. In this regard, in conjunction with a corresponding pair of stereoscopic eyeglasses worn by the surgeon, such displays facilitate depth perception in an image by presenting the image to the surgeon as a pair of distinct images separately provided to the left and right eyes, respectively. The pairs of images are created to replicate the effect of the offset between the left and right eyes, which results in a difference in what is seen in the display by each eye. The different images seen in the display by each eye are perceived as differences in the depths of the objects in the images. In some configurations, the stereoscopic display includes a film carefully aligned with the pixels of the display that, via the stereoscopic eyeglasses, enables certain pixel rows or columns to be visible by one eye and other pixel rows or columns to be visible by the other eye.

Although the above-described surgeon console and display scheme is adequate, it may be improved. In particular, with regard to viewing the surgical site via the stereoscopic eyeglasses and/or display, in many instances, each of the surgeon's eyes needs to be positioned in a specific location in order for the images to be perceived with minimal degradation. As such, the surgeon may be restricted as to his or her positioning within the console. Further, as some medical procedures may be relatively lengthy in duration, wearing stereoscopic eyeglasses and/or maintaining the restricted positioning within the console may cause discomfort for some surgeons.

SUMMARY

According to an aspect of the present disclosure, systems, methods and computer-readable media are provided that addresses the above-mentioned needs. In an aspect of the present disclosure, a system is provided for robotic surgical device control, including a robotic arm, an autosteroscopic display, a user image capture device, an image processor, and a controller. The robotic arm is coupled to a patient image capture device. The autostereoscopic display is configured to display an image of a surgical site obtained from the patient image capture device. The image processor is configured to identify a location of at least part of a user in an image obtained from the user image capture device. The controller is configured to, in a first mode, adjust a three dimensional aspect of the image displayed on autostereoscopic display based on the identified location, and, in a second mode, move the robotic arm or instrument based on a relationship between the identified location and the surgical site image.

In another aspect of the present disclosure, the autostereoscopic display of the system is further configured to include a plurality of pixels including even pixel columns and odd pixel columns. Each pixel column is disposed below a corresponding vertical lens. The vertical lenses corresponding to the even pixel columns are configured to permit the even pixel columns to be perceptible by a first eye of the user, and the vertical lenses corresponding to the odd pixel columns are configured to permit the odd pixel columns to be perceptible by a second eye of the user. In a further aspect of the present disclosure, the controller is further configured to adjust the image displayed on the autostereoscopic display by adjusting one or more of the plurality of pixels. In still a further aspect of the present disclosure, the image processor of the system is further configured to identify the locations of the first eye and the second eye of the user in the image obtained from the user image capture device, and the controller is further configured to adjust the one or more pixels of the plurality of pixels displayed on the autostereoscopic display based, in part, on the identified location of the first eye of the user or the identified location of the second eye of the user.

In another aspect of the present disclosure, the controller of the system is further configured to detect a location of an eye gaze of the user based on the locations of the first eye and the second eye of the user, to detect a change of the location of the eye gaze of the user to another location, and to move the robotic arm coupled to the patient image capture device based on the relationship between the location of the eye gaze and the surgical site image. In a further aspect of the present disclosure, the controller is further configured to, in response to the detected change of the location of the eye gaze of the user, calculate a velocity magnitude and direction at which to move the arm. In an alternative aspect of the present disclosure, to detect the change of the location of the eye gaze of the user, the controller is further configured to determine whether the detected change of the location of the eye gaze of the user is outside of a first predetermined range of distances from a predetermined location. In another aspect of the present disclosure, the controller is further configured to determine whether the detected change of the location of the eye gaze of the user is outside of a second predetermined range of distances that is greater than the first predetermined range of distances, and in response to the determination of the detected change of the location of the eye gaze of the user being outside of the second predetermined range of distances, causing the system to provide a notification.

In another aspect of the present disclosure, the controller is further configured to determine whether a eye gaze of the user in the image is held at the location for a time period that is greater than a threshold time period, and in response to the eye gaze being held for the time period greater than the threshold time period, move the robotic arm coupled to the patient image capture device.

In still another aspect of the present disclosure, the controller is further configured to detect an input to move the patient image capture device, determine a change in the identified location, determine a head position and/or velocity, based on the change in the identified location, and determine one or more of a head tilt, a head orientation, or a head roll, based on the determined head position and/or velocity.

In another aspect of the present disclosure, the patient image capture device is configured to achieve a first predetermined latency in capturing and transmitting to the image processor visual content, and the image processor comprises multiple sub-processors in parallel execution to achieve a second predetermined latency in processing the visual content, determining the location of the eye gaze of the user, and transmitting a control signal to the patient image capture device.

In yet another aspect of the present disclosure, the controller is further configured to determine a head pose, based on the identified location, calculate a translational velocity based on the determined head pose, map an x-coordinate from the calculated translational velocity to yield an in/out velocity, map a z-coordinate from the calculated translational velocity, calculate an YZ velocity of orientation based on the determined head pose, and map the calculated YZ velocity to yield a pan angular velocity, extract roll values from the determined head pose, map the extracted roll values to yield a roll angular velocity, and determine a pose of the patient image capture device, based on the in/out velocity, the pan angular velocity, and the roll angular velocity.

In still yet another aspect of the present disclosure, the robotic surgical device includes an endoscope.

In still yet another aspect of the present disclosure, the controller is configured to perform in both the first mode and the second mode concurrently.

In still yet another aspect of the present disclosure, the controller is configured to perform in the first mode and the second mode separately.

In another aspect of the present disclosure, a computer-implemented method is provided for robotic surgical device control. The method includes displaying an image of a surgical site obtained from a patient image capture device coupled to a robotic arm, identifying a location of at least a part of a user in an image obtained from the user image capture device, operating in a first mode by adjusting a three-dimensional aspect of the image displayed on an autostereoscopic display, based on the identified location, and operating in a second mode by moving the robotic arm coupled to the patient image capture device based on a relationship between the identified location and the surgical site image.

According to another aspect of the present disclosure, the autostereoscopic display is further configured to include a plurality of pixels including even pixel columns and odd pixel columns, each pixel column is disposed below a corresponding vertical lens, the vertical lenses corresponding to the even pixel columns are configured to permit the even pixel columns to be perceptible by a first eye of the user, and the vertical lenses corresponding to the odd pixel columns are configured to permit the odd pixel columns to be perceptible by a second eye of the user, and the method further includes adjusting the image displayed on the autostereoscopic display by adjusting one or more pixels of the plurality of pixels.

In another aspect of the present disclosure, the method further includes identifying the locations of the first eye and the second eye of the user in the image obtained from the user image capture device, and adjusting the one or more pixels of the plurality of pixels displayed on the autostereoscopic display based, in part, on the identified location of the first eye of the user of the identified location of the second eye of the user.

In another aspect of the present disclosure, the method further includes detecting a location of an eye gaze of the user based on the locations of the first eye and the second eye, detecting a change of the location of the eye gaze of the user to another location, and moving the robotic arm coupled to the patient image capture device based on the relationship between the location of the eye gaze and the surgical site image.

In still another aspect of the present disclosure, the method further includes, in response to the detected change of the location of the eye gaze of the user, calculating a velocity magnitude and direction at which to move the arm in the surgical site image.

In another aspect of the present disclosure, the method further includes detecting the change of the location of the eye gaze of the user by determining whether the detected change of the location of the eye gaze of the user is outside of a first predetermined range of distances from a predetermined location.

In another aspect of the present disclosure, the method further includes determining whether the location of the eye gaze of the user is outside of a second predetermined range of distances that is greater than the first predetermined range of distances, and in response to the location of the eye gaze of the user being outside of a second predetermined range of distances, causing the system to provide a notification.

In still another aspect of the present disclosure, the method further includes determining whether a eye gaze of the user is held at the location for a time period that is greater than a threshold time period, and in response to the eye gaze being held for the time period that is greater than the threshold time period, moving the robotic arm coupled to the patient image capture device.

According to still another aspect of the present disclosure, the method further includes detecting an input to move the patient image capture device, determining a change in the identified location, determining a head position and/or velocity, based on the change in the identified location, and determining one or more of a head tilt, a head orientation, or a head roll, based on the determined head position and/or velocity.

In yet another aspect of the present disclosure, the method further includes determining a head pose, based on the identified location, calculating a translational velocity based on the determined head pose, mapping an x-coordinate from the calculated translational velocity to yield an in/out velocity, mapping a z-coordinate from the calculated translational velocity, calculating an YZ velocity of orientation based on the determined head pose, and mapping the calculated YZ velocity to yield a pan angular velocity, extracting roll values from the determined head pose, mapping the extracted roll values to yield a roll angular velocity, and determining a pose of the patient image capture device, based on the in/out velocity, the pan angular velocity, and the roll angular velocity.

In still another aspect of the present disclosure, the method further includes performing both the first mode and the second mode concurrently.

In still yet another aspect of the present disclosure, the method further includes performing the first mode and the second mode separately.

According to another aspect of the present disclosure, a non-transitory computer-readable medium is provided having stored thereon instructions which, when executed by a processor, cause displaying an image of a surgical site obtained from a patient image capture device coupled to a robotic arm, identifying a location of at least a part of a user in an image obtained from the user image capture device, operating in a first mode by adjusting a three-dimensional aspect of the image displayed on an autostereoscopic display, based on the identified location, and operating in a second mode by moving the robotic arm coupled to the patient image capture device based on a relationship between the identified location and the surgical site image.

In an aspect of the present disclosure, the non-transitory computer-readable medium further includes instructions which, when executed by a processor, cause the autostereoscopic display which includes a plurality of pixels including even pixel columns and odd pixel columns, each pixel column is disposed below a corresponding vertical lens, the vertical lenses corresponding to the even pixel columns are configured to permit the even pixel columns to be perceptible by a first eye of the user, and the vertical lenses corresponding to the odd pixel columns are configured to permit the odd pixel columns to be perceptible by a second eye of the user, to adjust the image displayed on the autostereoscopic display by adjusting one or more pixels of the plurality of pixels.

In another aspect of the present disclosure, the non-transitory computer-readable medium further includes instructions which, when executed by a processor, cause identifying the locations of the first eye and the second eye of the user in the image obtained from the user image capture device, and adjusting the one or more pixels of the plurality of pixels displayed on the autostereoscopic display based, in part, on the identified location of the first eye of the user of the identified location of the second eye of the user.

In another aspect of the present disclosure, the non-transitory computer-readable medium further includes instructions which, when executed by a processor, cause detecting a location of an eye gaze of the user based on the locations of the first eye and the second eye, detecting a change of the location of the eye gaze of the user to another location, and moving the robotic arm coupled to the patient image capture device based on the relationship between the location of the eye gaze and the surgical site image.

In still another aspect of the present disclosure, the non-transitory computer-readable medium further includes instructions which, when executed by a processor, cause, in response to the detected change of the location of the eye gaze of the user, calculating a velocity magnitude and direction at which to move the arm in the surgical site image.

In still yet another aspect of the present disclosure, the non-transitory computer-readable medium further includes instructions which, when executed by a processor, cause detecting the change of the location of the eye gaze of the user further comprises determining whether the detected change of the location of the eye gaze of the user is outside of a first predetermined range of distances from a predetermined location.

In another aspect of the present disclosure, the non-transitory computer-readable medium further includes instructions which, when executed by a processor, cause, determining whether a eye gaze of the user is held at the location for a time period that is greater than a threshold time period, and in response to the eye gaze being held for the time period that is greater than the threshold time period, moving the robotic arm coupled to the patient image capture device.

In another aspect of the present disclosure, the non-transitory computer-readable medium further includes instructions which, when executed by a processor, cause, detecting an input to move the patient image capture device, determining a change in the identified location, determining a head position and/or velocity, based on the change in the identified location, and determining one or more of a head tilt, a head orientation, or a head roll, based on the determined head position and/or velocity.

In still another aspect of the present disclosure, the non-transitory computer-readable medium further includes instructions which, when executed by a processor, cause, determining a head pose, based on the identified location, calculating a translational velocity based on the determined head pose, mapping an x-coordinate from the calculated translational velocity to yield an in/out velocity, mapping a z-coordinate from the calculated translational velocity, calculating an YZ velocity of orientation based on the determined head pose, and mapping the calculated YZ velocity to yield a pan angular velocity, extracting roll values from the determined head pose, mapping the extracted roll values to yield a roll angular velocity, and determining a pose of the patient image capture device, based on the in/out velocity, the pan angular velocity, and the roll angular velocity.

In still another aspect of the present disclosure, the non-transitory computer-readable medium further includes instructions which, when executed by a processor, cause performing of both the first mode and the second mode concurrently.

In still yet another aspect of the present disclosure, the non-transitory computer-readable medium further includes instructions which, when executed by a processor, cause, performing the first mode and the second mode separately.

BRIEF DESCRIPTION OF THE DRAWINGS

The above and other aspects, features, and advantages of the present disclosure will become more apparent in light of the following detailed description when taken in conjunction with the accompanying drawings, in which:

FIG. 9 is a flow diagram of a method for controlling a robotic surgical system, in accordance with still yet another aspect of the present disclosure;

FIG. 10A is a graph mapping a velocity of a user's head and a velocity of a patient image capture device, in accordance with an aspect of the present disclosure;

FIG. 10B is a graph mapping a velocity of a user's head and a velocity of a patient image capture device, in accordance with another aspect of the present disclosure.

DETAILED DESCRIPTION

To provide enhanced visualization and control with improved comfort for the surgeon of a robotic surgical system, various systems and methods are described herein. In particular, the system is configured to continuously receive data related to movements of the surgeon and uses the movements to optimize the surgeon's user experience. For example, the surgeon's movements (obtained via eye-tracking, head-tracking or tracking of a portion of the surgeon's face) are used to identify a location of the surgeon. The identified location then may be used to determine whether the surgeon has moved, which, depending on a selected mode, may cause a three-dimensional aspect of an image displayed to be adjusted for optimal viewing for the surgeon and/or to move a robotic arm or instrument based on a relationship between the identified location and a surgical site image.

As used herein, the terms "clinician," "surgeon," "observer," generally refer to a user of an autostereoscopic display device described herein. Additionally, although the terms "first eye" and "second eye" are used herein to refer to a left eye and a right eye, respectively, of a user, this use is provided by way of example and should not be construed as limiting. Throughout this description, the term "proximal" refers to the portion of the device or component thereof that is farthest away from the patient and the term "distal" refers to the portion of the device or component thereof that is closest to the patient.

Figure 1:
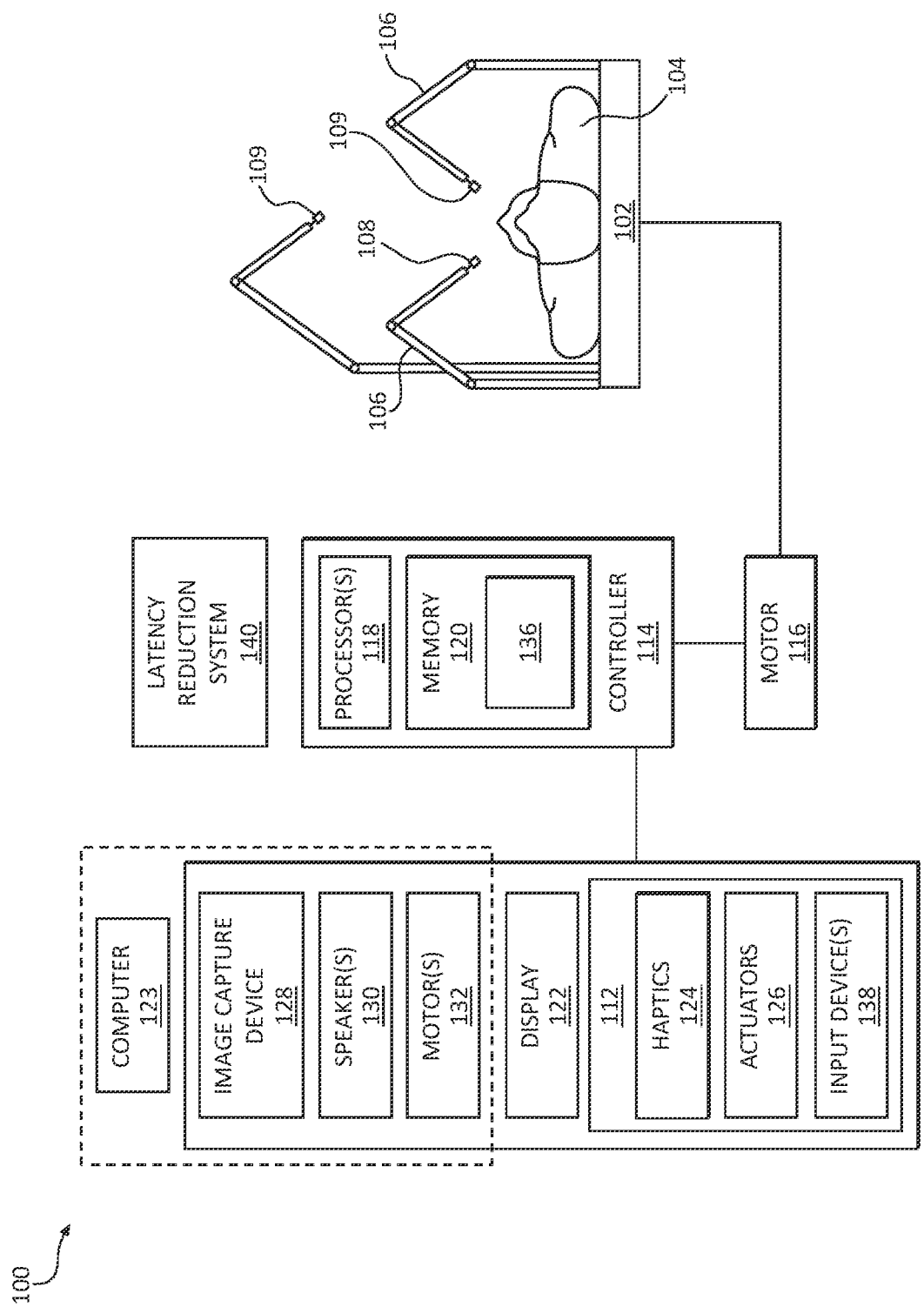
FIG. 1 is a diagram of an exemplary robotic surgical system including a stereoscopic display in accordance with an embodiment of the present disclosure.

FIG. 1 shows an exemplary robotic surgical system 100 that may be employed in accordance with various example embodiments herein. The specific number of components of the system 100 shown in FIG. 1 and the arrangement and configuration thereof are provided for illustrative purposes only, and should not be construed as limiting. For instance, various embodiments herein employ fewer or greater than all of the components shown in FIG. 1. Additionally, the exemplary robotic surgical system 100 depicted in FIG. 1 is provided as an example context in which various example embodiments herein are applicable. However, the various example embodiments herein are also applicable in contexts other than robotic surgical systems, for instance, in general stereoscopic display contexts.

The system 100 includes an operating table 102 upon which a patient 104 lies during a surgical procedure, robotic arms 106 having corresponding surgical instruments 108 interchangeably fastened thereto, a console 110 having handles 112 with which a clinician (also referred to herein as a "user") interacts during the surgical procedure, and a controller 114 and one or more motors 116 by which the console 110 is coupled to the robotic arms 106, surgical instruments 108, and image capture devices 109. The robotic arms 106 are each affixed to a corresponding base arranged adjacent to the operating table 102 and/or within range of the patient 104 undergoing the surgical procedure.

The controller 114 includes one or more processors 118 and memories 120, and may be integrated with the console 110 or provided as a standalone device within the operating theater. As described in further detail below, the processor 118 executes instructions 136 (in an example, software) stored in the memory 120 to perform procedures of the various embodiments herein. As will be appreciated, the processor 118 and memory 120 implementation is provided by way of example only, and should not be construed as limiting. For instance, procedures of any of the embodiments of the present disclosure may be implemented by hardware components, firmware components, software components, and/or any combination thereof.

During operation of the surgical system 100, the handles 112 are moved by the clinician to produce a corresponding movement and/or actuation of the working ends of the robotic arms 106 and/or surgical instruments 108. The handles 112 provide a signal to the controller 114 which then provides a corresponding signal to one or more drive motors 116. The one or more drive motors 116 are coupled to the robotic arms 106 in order to move the robotic arms 106 and/or surgical instruments 108.

The handles 112 may include various haptics 124 to provide feedback to the clinician relating to various tissue parameters or conditions, in an example, tissue resistance due to manipulation, cutting, or otherwise treating, pressure by the instrument onto the tissue, tissue temperature, tissue impedance, etc. As can be appreciated, such haptics 124 provide the clinician with enhanced tactile feedback simulating actual operating conditions. The haptics 124 may include vibratory motors, electroactive polymers, piezoelectric devices, electrostatic devices, subsonic audio wave surface actuation devices, reverse-electrovibration, or any other device capable of providing a tactile feedback to a user. The handles 112 may also include a variety of different actuators 126 for delicate tissue manipulation or treatment further enhancing the clinician's ability to mimic actual operating conditions.

In addition to the handles 112, the console 110 includes one or more input devices 138 for receiving inputs from the user. For example, the input devices 138 include, but are not limited to, a touchscreen, a mouse, a keyboard, a joystick, or any other device suitable for communicating inputs from the user to the system 100. In an embodiment, the input devices 138 are configured to permit the user to make selections displayed on an autostereoscopic display device 122 (also referred to herein as "autostereoscopic display" or simply a "display") or on a touchscreen (if included), such as from drop down menus, pop-up windows, or any other presentation mechanisms. In another embodiment, the input devices 138 are configured to permit the user to manipulate a surgical site image, such as by zooming in or out of the surgical site image, selecting a location on the surgical site image, and the like.

The surgical instruments 108 may be any type of surgical instrument, such as, by way of example and not limitation, an image capture device 109, an end effector, a grasper, a knife, scissors, and/or the like. The image capture device 109 is configured to capture stereoscopic images of the surgical site and may be a camera or a probe that includes a stereoscopic image capture device. Suitable probes configured to be patient image capture devices include, but are not limited to, endoscopes and the like. The probe is inserted into a patient in order to capture a stereoscopic image of a region of interest inside the patient during a surgical procedure. In accordance with some embodiments herein, the stereoscopic images captured by the image capture device are communicated to the autostereoscopic display 122 of the console 110 that displays the images to the clinician.

Figure 4:
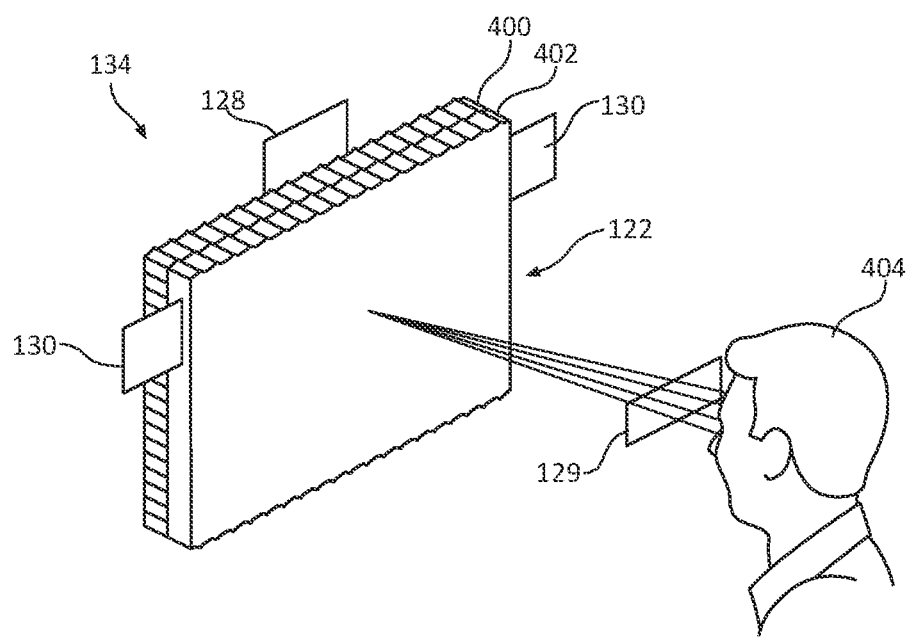
FIG. 4 is a simplified diagram of the stereoscopic display of FIG. 1, in accordance with another aspect of the present disclosure.

As described in further detail below, in some exemplary embodiments herein the console 110 includes an image capture device 128 (in an example, one or more cameras) that captures one or more images of the user (not shown in FIG. 1). For example, the image capture device 128 may be configured to periodically capture still images of the user, video of the user, and the like. In another embodiment, the image capture device 128 is used to track the eyes, the face, the head or other feature(s) of the user. In this regard, tracking can be enhanced with the use of a wearable 129 worn by the user (as depicted in FIG. 4) to provide fixed locations that may be detected when images of the user are processed. The wearable 129 may be provided in the form of glasses, a headband, a set of markers placed on locations on the user or another configuration. The image capture device 128 can be integrated with, and/or positionally fixed to, the display 122, such that the positional relationship between the image capture device 128 and the display 122 is known and can be relied upon by the processor(s) 118 in various computations. In another example, the processor(s) 118 utilizes the images captured by the image capture device 128 to determine a position of the user, for example, by employing a recognition and tracking algorithm that compares the determined position of the user to a predetermined position criterion. The processor(s) 118 cause a message to be generated based on a result of the comparing to be provided to the user, for example, visibly by way of the display 122, audibly by way of one or more audio devices (in an example, speakers) 130, and/or through tactile feedback by way of the handles 112. Providing the user with such a message can, if warranted, inform the user on how to move to a position that is more optimal for improved perception of autostereoscopic visual content.

In order to further improve user perception of the autostereoscopic visual content, the system 100 includes a latency reduction system 140 that is configured to reduce a lag time between images of the user captured by the image capture device 128 and/or the images captured of the surgical site by the image capture device 109. In an embodiment, the processor(s) 118 communicate with or include the latency reduction system 140. In an embodiment, the processor(s) include one or more sub-processors operating in parallel to permit the latency reduction system 140 to meet latency targets of <about 60 milliseconds (ms). In accordance with an embodiment, the latency reduction system 140 employs a green screen in which a graphical user interface is overlaid on top of the video stream captured by the image capture device 109 of the surgical site. Such an embodiment does not employ digital manipulation and hence, image enhancements, conversion into an autostereoscopic format, and remote viewing or recording are not implemented. In another embodiment, the latency reduction system 140 includes additional components either implemented into or in communication with the controller 114 or the autostereoscopic display system 134 for minimizing the latency between real-time head, eye, and/or facial movements and the display of surgical site images and overcomes the deficiencies of the previously-described embodiment.

Figure 2:
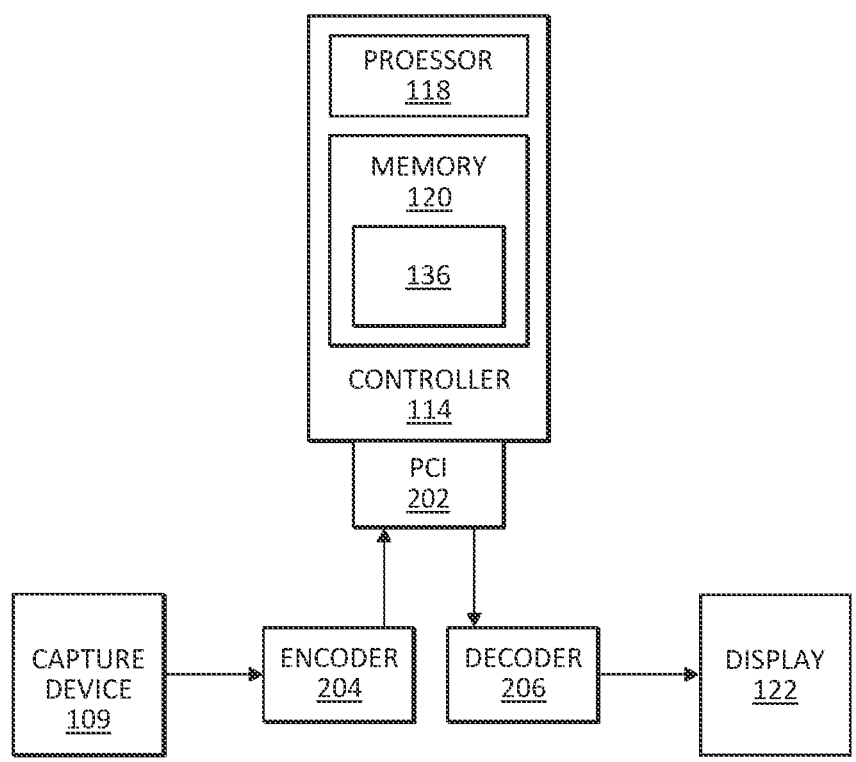
FIG. 2 illustrates a latency reduction system, in accordance with an aspect of the present disclosure, for use with the stereoscopic display shown in FIG. 1.

FIG. 2 is a block diagram of the latency reduction system 140 as implemented into the tower of the system 100, according to an aspect of the disclosure. The latency reduction system 140 includes a peripheral component interconnect (PCI) card 202, an encoder 204, and a decoder 206, which are coupled to the controller 114 of FIG. 1, in accordance with an embodiment. Although illustrated as separate components, it will be appreciated that two or more of the PCI card 202, the encoder 204, and the decoder 206 may be configured as a single component, in other embodiments.

During operation, the image capture device 109, such as an endoscope, transmits video to the encoder 204. The encoder 204 processes the video into encoded image data thereby translating the video into a desired format. After processing, the encoded image data is transmitted to the PCI card 202, which manipulates and composites the image data. In an embodiment, the data then is further communicated to the controller 114 to be transmitted as image data to a display (not shown) for viewing by users in the operating room or stored in the memory 120 for later processing. In another embodiment, the encoded image data is communicated from the PCI card 202 to the decoder 206, which decodes the image data in order to translate the image data into its original format, for example, video. Next, the video is then transmitted to the display 122 for display.

To enhance the video, a graphical user interface is overlaid onto the video either by the controller 114 or by the computer 123. The image capture device 128 on the display 122 tracks the position of the user, and data related to the user's position is transmitted back to the controller 114 to create a desired video format for the display 122, in an embodiment. As such, the transmission of the tracked position of the user is sent over Ethernet or via another low latency communication protocol. The above-described architecture allows the image processing, compositing and/or formatting of the images from the image capture devices 109, while taking into account positional data corresponding to the user derived from images captured by the user image capture device 128.

Figure 3:
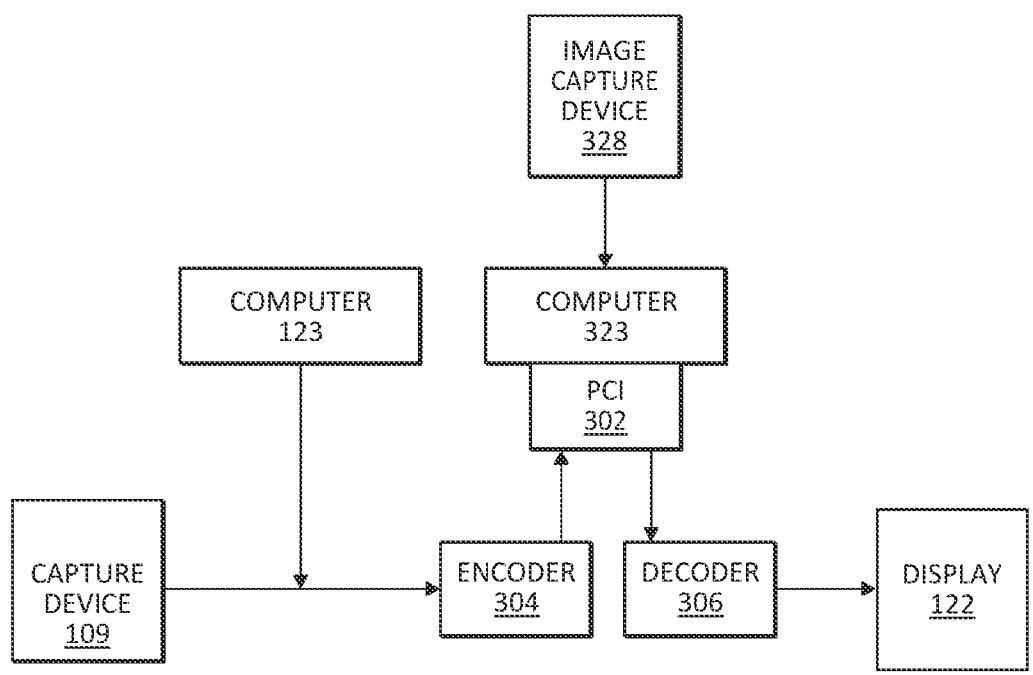
FIG. 3 illustrates a latency reduction system, in accordance with another aspect of the present disclosure, for use with the stereoscopic display shown in FIG. 1.

FIG. 3 is a block diagram illustrating the latency reduction system 140 as included in the autostereoscopic display system 134 of FIG. 1, according to another aspect of the disclosure. Here, the latency reduction system 140 includes a peripheral component interconnect (PCI) card 302, a computer 323, an encoder 304, a decoder 306, and optionally, an image capture device 328. As will be appreciated, two or more of these components may be configured as a single component, in some embodiments. The encoder 304 receives video from the image capture device 109, in video format, and data from the computer 123. The received video is converted into encoded image data, for example, data in a desired format for processing by the computer 323. The encoded image data is then provided to the PCI card 302 coupled to the computer 323. The computer 323 may receive additional image data from the image capture device 328, which may capture video (in a format suitable for processing by the computer 323) of the user for user location identification purposes. In an embodiment, a head-tracking, eye-tracking or facial-tracking algorithm is applied to the captured video of the user, and the outcome is used in modifying and formatting of the encoded image data. The modified encoded image data is then sent to the decoder 306, which then decodes and further formats the image data into its original format. The decoded image data is then provided as video to the display 122 for display. Similar to the architecture described in relation to FIG. 2, the above-described architecture also allows image processing, compositing and/or formatting of the images from the image capture devices 109, while taking into account positional data corresponding to the user derived from images captured by the user image capture device 328.

Returning to FIG. 1, the console 110 also includes one or more motors 132 configured to reposition the display 122, and the processor 118 is configured to determine a position of the user based on the captured image of the user, compare the determined position of the user to a predetermined position criterion, and cause the motors 132 to reposition the display 122 based on a result of the comparing. The one or more motors 132 can be single-axis motors or multiple-axis (in an example, 3 axis) motors that facilitate repositioning of the display 122 along a single axis or along multiple axes, respectively. Repositioning the display 122 based on user position can enable the display 122 to maintain a position, relative to the user, that is more optimal for improved perception of stereoscopic visual content.

Figure 5:
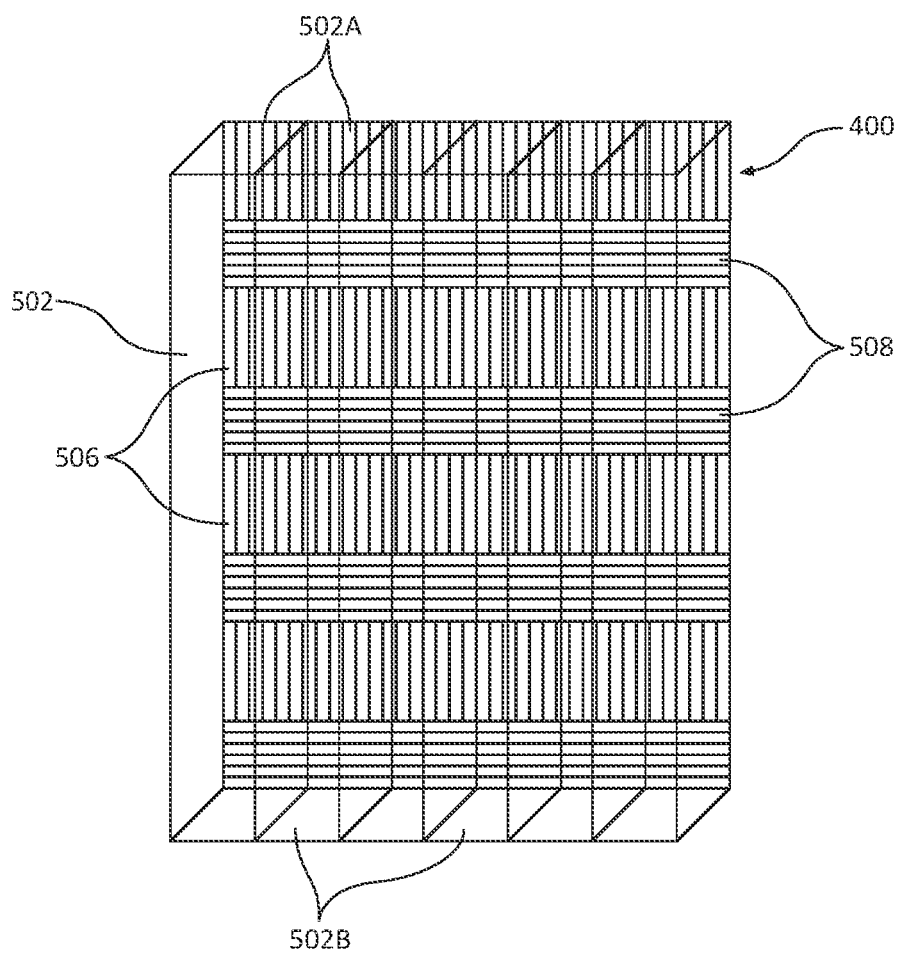
FIG. 5 is a close-up view of a portion of the stereoscopic display of FIG. 4, in accordance with an aspect of the present disclosure.

Certain components of the system 100 (for example, components 120, 122, 128, 130, and/or 132) may represent an autostereoscopic display system 134 in accordance with some example embodiments herein. Reference will now be made to FIG. 4 and FIG. 5, which illustrate additional aspects of the example autostereoscopic display system 134 and the autostereoscopic display 122 thereof. The specific number of components of the system 134 shown in FIG. 4 and FIG. 5, and the arrangement and configuration thereof, are provided for illustrative purposes only, and should not be construed as limiting. For instance, some embodiments herein employ fewer or greater components than the components shown in FIG. 4 and FIG. 5. Additionally, for clarity, some components of the system 134 are omitted from FIG. 4 and FIG. 5. Further, the autostereoscopic display system 134 herein is also applicable in contexts other than robotic surgical systems, for instance, in general autostereoscopic display contexts.

FIG. 4 includes a perspective view of a portion of the autostereoscopic display system 134, showing an exemplary arrangement of the autostereoscopic display 122, the image capture device 128, the audio devices 130, the motor(s) 132, in accordance with various embodiments herein. The display 122 includes a screen 400 and a lenticular lens layer 402 disposed in front of the screen 400. The screen 400 includes pixels that direct visual content displayed by certain pixels to certain eyes of the user 404 by way of the lenticular lens layer 402. In particular, as depicted in FIG. 5, the screen 400 includes a first set of pixels 506 (in an example, odd pixel columns) of the autostereoscopic display 122 and a second set of pixels 508 (in an example, even pixel columns) of the autostereoscopic display 122. The lenticular lens layer 502 includes a plurality of vertical lenses 502a, 502b disposed over corresponding pixel columns. For example, the first set of pixels 306 (for example, the odd pixel columns) are overlayed with one or more of the vertical lenses 502a which are configured to be directed at an angle suitable to permit the visual content of the first set of pixels 506 to be perceived by the first eye of the user. The second set of pixels 508 (for example, the even pixel columns) are overlayed with one or more of the vertical lenses 502b that are configured to be directed at an angle suitable to permit the visual content of the second set of pixels 308 to be perceived by the second eye of the user.

Figure 6:
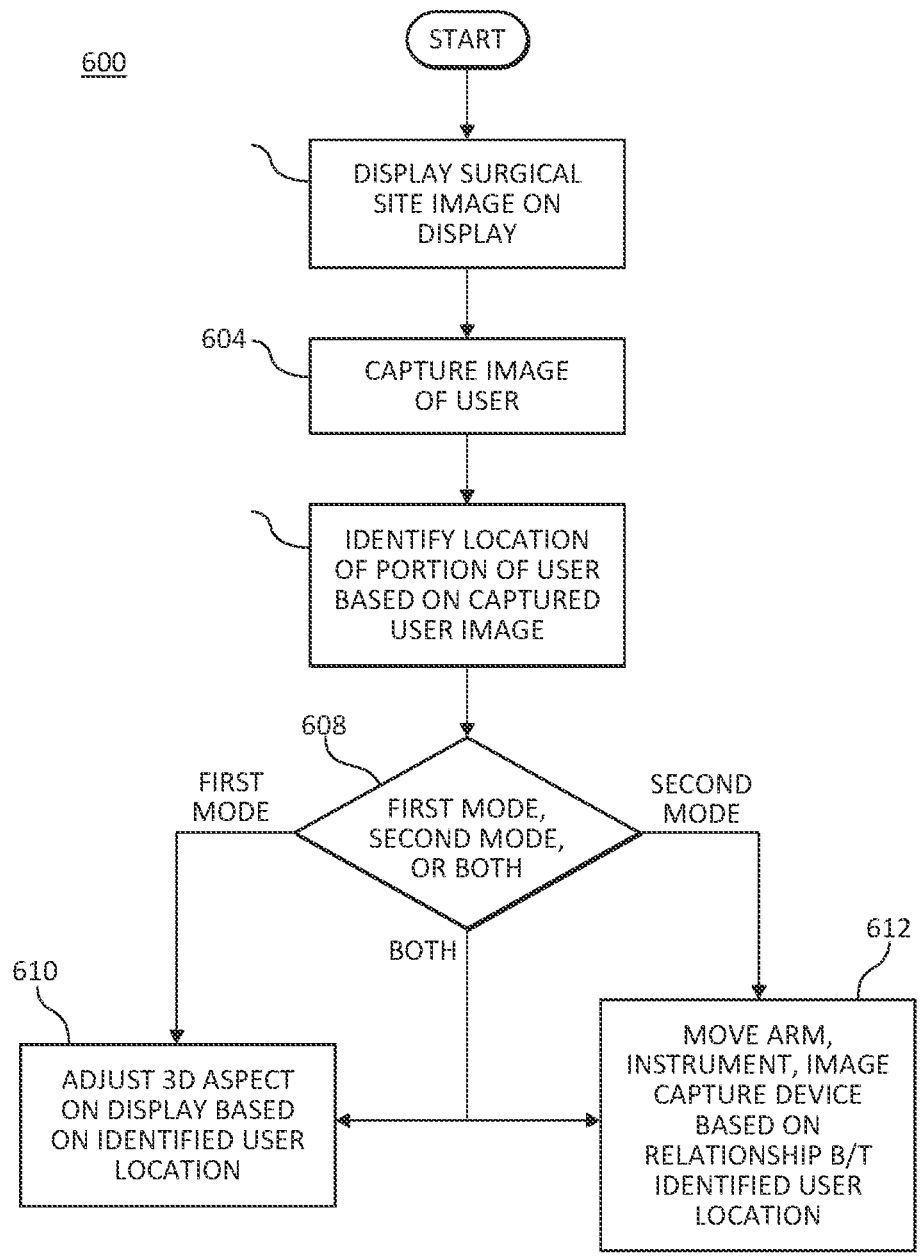
FIG. 6 is a flow diagram of a method for controlling a robotic surgical system, in accordance with an aspect of the present disclosure.

Having described an exemplary autostereoscopic display system 134, reference will now be made to FIG. 6, which depicts an exemplary computer-implemented procedure 600 for controlling the autostereoscopic display system 134, in accordance with an embodiment herein. According to an embodiment, the robotic surgical system 100 may be operated in a first mode, in which three-dimensional aspects of the autostereoscopic display system 134 are adjusted, or in a second mode, in which a relationship between a user location and a surgical site image is used to move the robotic arm 106 and/or the patient image capture device 109 coupled to the robotic arm 106. The procedure 600 may be implemented, at least in part, by the processor 118 executing instructions 136 stored in the memory 120 (FIG. 1). Additionally, the particular sequence of steps shown in the procedure 600 of FIG. 6 is provided by way of example and not limitation. Thus, the steps of the procedure 600 may be executed in sequences other than the sequence shown in FIG. 6 without departing from the scope of the present disclosure. Further, some steps shown in the procedure 600 of FIG. 6 may be concurrently executed with respect to one another instead of sequentially executed with respect to one another.

In accordance with an embodiment, the procedure 600 includes displaying a surgical site image on an autostereoscopic display 122 at block 602. For example, the image capture device 109 coupled to the robotic arm 106 is positioned within the surgical site and an image of the surgical site is captured by the image capture device 109. The controller 114 transmits signals representing the captured image of the surgical site to the autostereoscopic display 122 and the autostereoscopic display 122 displays the surgical site image.

At some time during which the user is observing the autostereoscopic display 122, the image capture device 128 coupled to the autostereoscopic display 122 captures an image of the user at block 604. As noted above, the image capture device 128 captures a series of images, such as in a video format, or periodically captures still images of the user.

A location of one or more features of the user is identified from the captured user image at block 606. In an example, the one or more features of the user includes features of the user's face, such as the user's forehead, chin, nose, right eye, left eye, a location in between the user's eyes, or other features of the user. In another example, the one or more features of the user for identifying location is the user's head. Detecting the location of one or more features of the user may be further enhanced by the use of the wearable 109 (for example, glasses, a head band, stickers or other wearable placed on the user). In such implementation, the wearable 109 includes one or more markers that may be detected in the images of the user and the markers may be used to establish the location of the portion of the user. In an embodiment, a suitable algorithm for the recognition and tracking of the selected feature of the user is applied to the captured series of images. For example, an eye-tracking or head-tracking algorithm is used to track the eyes or head of the user at all times during the use of the robotic surgical system 10. Data related to the tracked selected feature of the user is stored in a memory 120.

At block 608, a determination is made as to whether a selection of a first mode of operation, a second mode of operation, or both has been received. The selection may be received via the input device 138. If a selection for the first mode of operation has been received, the procedure 600 proceeds to block 610, in which the three-dimensional aspect on the autostereoscopic display 122 is adjusted based on the identified user location obtained at block 606. In an embodiment, the location of the user is identified by detecting positioning of the first eye and the second eye of the user, which is determined from eye-tracking algorithms for calculating the location of the first and second eyes of the user.

Alternatively, the location of the user is identified by detecting positioning of the user's head. Similar to eye-tracking technologies, head-tracking fixes a location on the user's head and suitable algorithms calculate the location based on the fixed location on the user's head.

The adjustment of the three-dimensional aspect is performed by adjusting portions of the image shown in the alternating pixel columns based on the user moving from a first spatial location in front of the display 122 to a second spatial location. For example, one or more of the pixels in the odd pixel columns to be perceived by the left eye of the user are adjusted and/or one or more of the pixels in the even pixel columns to be perceived by the right eye of the user are adjusted. As a result, the corresponding vertical lenses 402*a* disposed over the odd pixel columns permit the left eye to perceive the corresponding change in the image, and the vertical lenses 402*b* disposed over the even pixel columns permits the right eye to perceive the corresponding change in the image. Block 610 continuously iterates as the identified user location changes at block 606.

If a selection for the second mode of operation has been received, the procedure 600 proceeds to block 612. At block 612, the robotic arm 106, the instrument 108, or image capture device 109 is moved, based on a relationship between the identified user location obtained at block 606 and the surgical site image displayed at block 602. Returning to block 608, if a selection for both the first and second modes is received, the procedure 600 performs the operations in blocks 610 and 612, either sequentially or concurrently.

Figure 7:
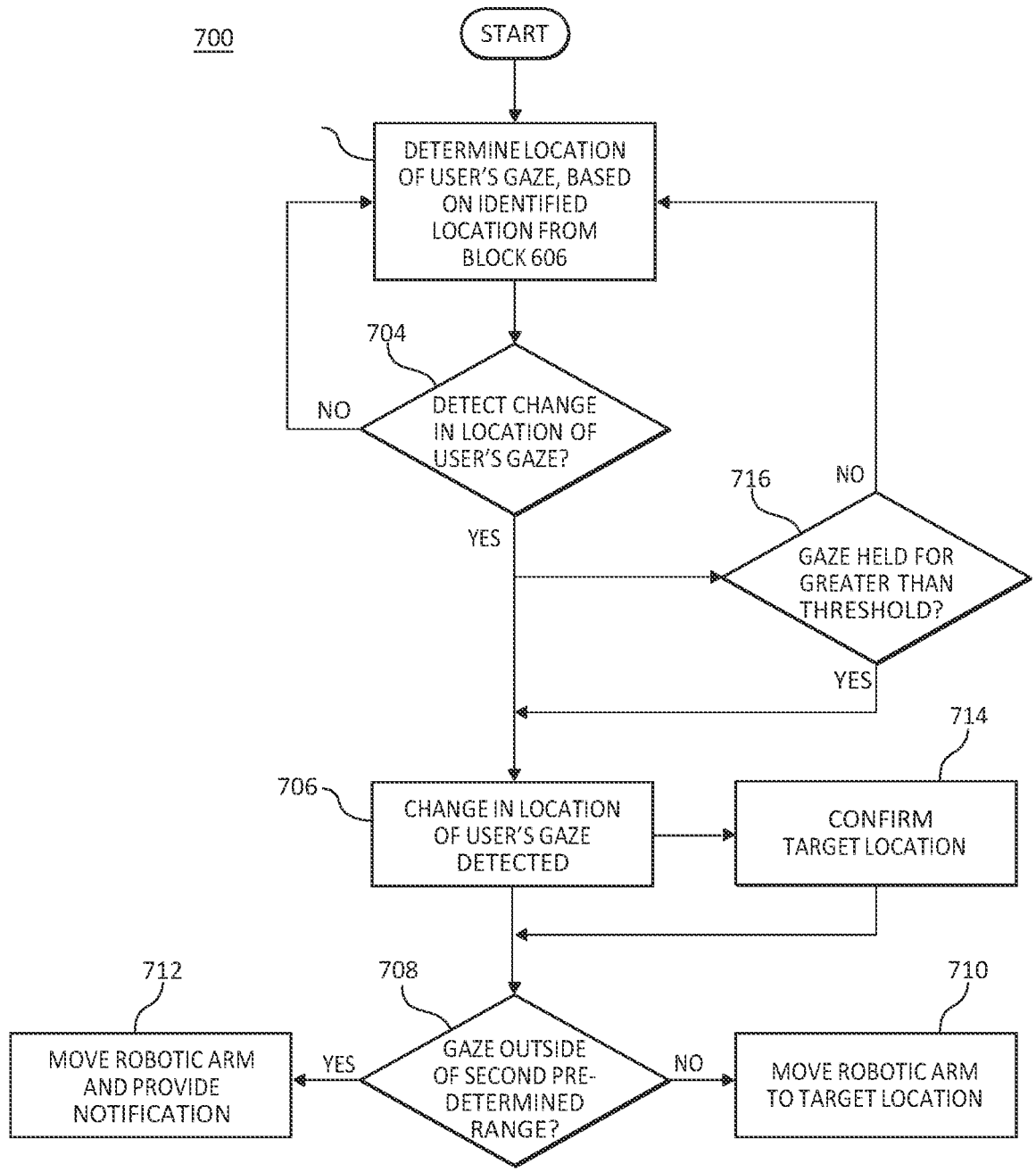
FIG. 7 is a flow diagram of a method for controlling a robotic surgical system, in accordance with another aspect of the present disclosure.

FIG. 7 is an exemplary computer-implemented procedure 700 for controlling the robotic arm 106, and in particular, the image capture device 109 coupled to the robotic arm 106, based on the relationship between the identified user location and the surgical site image described in block 612 of procedure 600, wherein the identified user location is based upon the user's eye gaze, accordance with another embodiment. The procedure 700 may be implemented, at least in part, by the processor 118 executing instructions 136 stored in the memory 120 (FIG. 1). Additionally, the particular sequence of steps shown in the procedure 700 of FIG. 7 is provided by way of example and not limitation. Thus, the steps of the procedure 700 may be executed in sequences other than the sequence shown in FIG. 7 without departing from the scope of the present disclosure. Further, some steps shown in the procedure 700 of FIG. 7 may be concurrently executed with respect to one another instead of sequentially executed with respect to one another.

At block 702, the location of the user's eye gaze is determined based on the identified location of the user, for example, from block 602 of procedure 600. In an embodiment, the user's eye gaze is the location of the user's pupil's when looking at an object with the user's eyes, for example, when the user's eyes are focused at a point on a screen the user is focused on. The identified location of the user may include the location of the first eye and the second eye from the captured image of the user. In this regard, any one of various algorithms suitable for calculating a location of the user's eye gaze from the captured image of the user is employed. For example, the location of the user's eye gaze may be determined from applying eye-tracking algorithms to image data including a series of the captured images of the user (for example, a video taken of the user including, among other things, the user's eyes) and the location of the eyes can be determined therefrom.

A determination is then made as to whether a change in the location of the user's eye gaze is detected at block 704.

In an embodiment, a first location of the user's eye gaze at a first time instance is compared with a second location of the user's eye gaze at a second time instance. For example, the first location of the user's eye gaze may be obtained from captured video of the user at a first time instance, and the second location of the user's eye gaze may be obtained from the same captured video after a lapse of time (e.g., at a second time instance). If a difference in the distance between the two locations at the two time instances is greater than a threshold distance, a change in location is detected and the procedure 700 continues to block 706. If the difference in the distance is less than the threshold distance, the operation in block 704 is reiterated and no change in location is detected.

In another example of the operation at block 704, a determination is made as to whether the user's eye gaze is outside of a first predetermined range of distances. The first predetermined range of distances may include a range of acceptable distances from an initial eye gaze location (also referred to as part of a "dead zone") which does not trigger detection of a change in location of the user's eye gaze. It will be appreciated that in embodiments in which a view of the image can be zoomed in or out, the particular distances included in the first predetermined range of distances may be scaled accordingly. In another embodiment, the first predetermined range of distances may be of acceptable distances adjacent the initial eye gaze location. For example, an input indicating the selected location may be received via the input device 138. If the determination is made that the user's eye gaze is not outside of the first predetermined range of distances, control is passed back to block 702. If the determination is made that the user's eye gaze is outside of the first predetermined range of distances, control is passed to block 706, where a change in the location is detected.

In response to the detected change in location, a determination is made as to whether the user's eye gaze is outside of a second predetermined range of distances at block 708. Specifically, the second predetermined range of distances may include a range of distances the eye would move, which would correspond to the user's eye gaze being outside of the image displayed on the display 122 of the autostereoscopic display device 134. For example, the second predetermined range of distances may include distances that include and are outside an outer perimeter of the image displayed on the display 122.

If the determination is made that the user's eye gaze is not outside of the second predetermined range of distances, the procedure continues to block 710. At block 710, the robotic arm 106 moves the patient image capture device 109 to a target location within the surgical site corresponding to the location on the image displayed on the autostereoscopic display at which the user's eye gaze is directed from block 704. In this regard, a velocity magnitude and a direction in which to move the robotic arm 106 is calculated, based on the change in the location of the user's eye gaze. For example, the patient image capture device 109 is configured to achieve a first predetermined latency in the capturing and transmitting to the computer 323 visual content. In an embodiment, the first predetermined latency is in a range of less than about 60 ms. The computer 323 includes multiple sub-processors in parallel execution to achieve a second predetermined latency in processing the visual content, for example, digitization, determining the location of the user's eye gaze, and transmitting a control signal to the patient image capture device 109. The second predetermined latency is in a range of about less than about 40 ms. The robotic arm 106 moves the patient image capture device 109 to a position such that the image displayed on the autostereoscopic display 122 permits the user's eyes to focus at the center of the image. In an embodiment, a total amount of latency permitted for the robotic arm 106 to move into position from the moment the user's eye gaze has changed location is less than about 100 ms.

Returning to block 708, if the determination is made that the user's eye gaze is outside of the second predetermined range of distances, the procedure continues to block 712. At block 712, in response to the determination that the user's eye gaze is outside of the second predetermined range of distances, the robotic arm 106 continues to move the patient image capture device 109 at a velocity and in the direction corresponding to the direction and distance of the user's eye gaze. A notification may be provided that the movement of the patient image capture device 109 will stop when the user's eye gaze returns to within the second predetermined range of distances. Notification is indicated visually, for example, via vectors or arrows displayed on the autostereoscopic display 122 or by textual instructions, audibly by voice commands from speakers 130, or tactilely, such as through vibrations transmitted to the user via the input handles 112. In an embodiment in which vectors or arrows are displayed, a length of the arrow increases as the patient capture image device 109 moves further away from an original location, such as the center of the autostereoscopic display 122, while the length of the arrow decreases as the patient capture image device 109 moves closer to the original location.

In addition to the operations described above, the procedure 700 may include additional operations, in other embodiments. For example, in accordance with an embodiment, a confirmation of the target location within the surgical site is performed at block 714, prior to performing the operation of block 708. The target location is represented by an image captured from a second image capture device different than image capture device 109. The target location may be a location adjacent to the surgical site or stored in a database in the memory 120 and is displayed on a portion of the autostereoscopic display 122, such as in a pop-up window, or on a touchscreen serving as the input device 138. An input is received confirming that the displayed image corresponds to the target location within the surgical site. In an embodiment, confirmation is received via an input into the input devices 138 (for example, on the touch screen, if included, by the pressing of a button on a keyboard or clicking of the mouse). In another embodiment, confirmation is received via a gesture detected in the captured image of the user. For example, suitable algorithms may be implemented that identify particular eye gestures, such as blinking or closing of the eyes.

In accordance with another embodiment, in conjunction with determining whether the user's eye gaze location is outside of the first predetermined range of distances at block 706, a determination is made as to whether the user's eye gaze is held at the location for a duration that is greater than a threshold time period at block 716. The amount of time less than the threshold time period may also be part of the dead zone, which provides the user with a buffer permitting eye movement between locations without triggering detection of a changed location of the user's eye gaze. If the eye gaze is held at the location for a duration that is not greater than the threshold time period, the procedure 700 iterates at block 702. If the eye gaze duration is greater than the threshold time period, the procedure 700 proceeds to block 706 where a change in location is detected.

Figure 8:
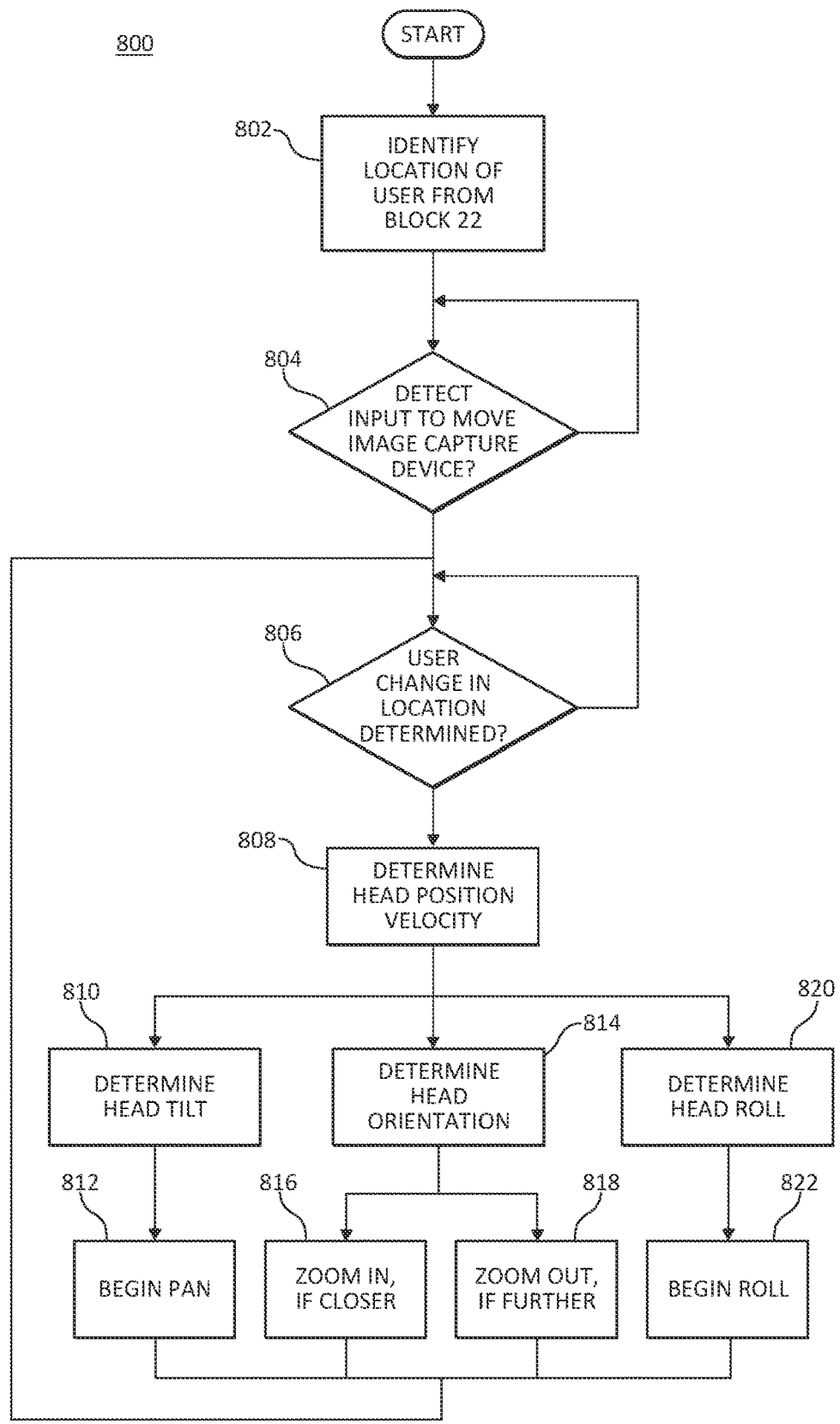
FIG. 8 is a flow diagram of a method for controlling a robotic surgical system, in accordance with still another aspect of the present disclosure.

FIG. 8 is an example computer-implemented procedure 800 for controlling the robotic arm 106, and in particular, movement of the patient image capture device 109 coupled to the robotic arm 106, based on the relationship between the identified user location and the surgical site image described in block 612 of procedure 600, in accordance with another embodiment. The procedure 800 may be implemented, at least in part, by the processor 118 executing instructions 136 stored in the memory 120 (FIG. 1). Additionally, the particular sequence of steps shown in the procedure 800 of FIG. 8 is provided by way of example and not limitation. Thus, the steps of the procedure 800 may be executed in sequences other than the sequence shown in FIG. 8 without departing from the scope of the present disclosure. Further, some steps shown in the procedure 800 of FIG. 8 may be concurrently executed with respect to one another instead of sequentially executed with respect to one another.

At block 802, a location of the user is identified, for example, from block 602 of procedure 600. In an embodiment, the user's location is identified from images of the user captured by the image capture device 128. For example, video or a series of images are taken of the user via the image capture device 128, and a tracking algorithm for tracking a fixed location on the user (such a location on the user's head or the user's eyes) is applied to video or a series of images taken of the user.

A determination is then made as to whether an input to move the patient image capture device 109 is detected at block 804. The input may be received from the input device 138, for example, by the user depressing a button, providing input to a mouse, or selecting an icon on a touchscreen. Alternatively, the input may be received by the detection of a gesture made by the user and identified from the video or series of images taken of the user by the image capture device 128. If no input is detected, block 804 is repeated. If input is detected, the procedure 800 proceeds to block 806.

Next, a change in location of the user is determined at block 806. In an embodiment, the change in location of the user is detected in the tracked location of the user. For example, any change in the positioning of the user's head, such as a change in an x-, y-, or z-coordinate location, or a change in roll, pitch or yaw, may be considered a change in the location of the user. The change in the location of the user may be determined by comparing a location of the user at a first time instance, for example at block 802, with a location of the user at a second time instance at block 806. According to an embodiment, the location of the user at the first time instance is taken from a first frame in a series of images or in a video of the user, and the location of the user at the second time instance is taken from a subsequent frame in the series of images or the video of the user. To determine whether the change in the location of the user is an intended action, in an embodiment, a determination may be made as to whether the change in the location of the user was maintained for a duration that is greater than a threshold time period, such as one (1) second or more. In another embodiment, in addition or alternatively, a determination is made as to whether the change in the location of the user is outside of a predetermined range of distances from an initial location of the user. In still another embodiment, in addition or alternatively, a determination is made as to whether a rate at which the user's change in location occurs is above a threshold rate. If the location of the user is either within the predetermined range of distance from an initial location or the rate of the user's change in location occurs below the threshold rate (in other words, falls within a "dead zone"), the change in the location of the user is not detected as an intended action. If the change in location of the user is determined, the method 800 continues to block 808. If no change in location is determined, the operation in block 806 is reiterated.

If the change in location of the user is detected, a determination of the user's head position and/or velocity is made at block 808. In particular, from data extracted using the images or the video of the user, calculations are made to determine the user's head position and/or velocity to thereby obtain a speed, distance, and direction of the user's head movement. Various aspects of the user's head movement may be obtained from the determined head position and/or velocity. Additionally, the aspects of the user's head movement may be mapped to the movement of the patient image capture device 109 and/or the manipulation of the images captured by the device 109. For example, positioning of the head may be mapped to positioning of the patient image capture device 109, and velocity of the head may be mapped to positioning of the patient image capture device 109.

In an embodiment, a user's head tilt is obtained from the determined head position and/or velocity at block 810. Head tilt is the motion made when the user moves his or her head left and/or right similar to when shaking the head "no." Head tilt may be used to initiate panning at block 812. Blocks 806, 808, 810, and 812 are reiterated until at 806, no change in location of the user is detected.

The user's head position and/or velocity can also be used to determine head orientation at block 814. Specifically, data is used to calculate whether the head is closer or farther away from an initial position and the speed at which the head movement was made. Algorithms are then applied to the data and the output causes zooming in at block 816 or zooming out at block 818 from a target location in a currently-displayed image. In an example, the target location may be a center of the currently-displayed image so that if the head has been moved closer relative to a fixed location (for example, a vertical plane within which the display 122 lies), then the image is zoomed in, either by moving the patient image capture device 109 closer to the target location or by magnifying the image at the target location, at block 816. Likewise, if the head has been moved farther away relative to the fixed location, then the image is zoomed out at block 818. The speed at which the zooming in or out occurs may be scaled. For instance, the speed of the change in head orientation may be directly proportional to the distance zoomed. Alternatively, other scaling may be implemented. Additionally, mechanisms may be included such that the user may select the scaling of the head orientation speed relative to the zooming speed. Blocks 806, 808, 810, 814, 816 and/or 818 are reiterated until at 806, no change in location of the user is detected.

At block 820, head roll may be determined from the user's head position and/or velocity as well. Head roll is the motion made when the user rotates his or her head to move the right ear closer to the right shoulder or the left ear closer to the left shoulder. In an embodiment, the movement of the head roll may be mapped to moving the patient image device 109 in a rolling motion at block 822. For example, in embodiments in which the patient image device 109 includes an angled distal end, rotating the angled distal end relative to a longitudinal axis of the patient image device 109 can be controlled using head rolling. Blocks 806, 808, 810, 820, and 822 are reiterated until at 806, no change in location of the user is detected.

In many cases, two or more of the aspects obtained from the user's head position and/or velocity are combined such that calculations may be combined to provide combined outputs, as illustrated in a flow diagram of a procedure 900 in FIG. 9. The procedure 900 may be implemented, at least in part, by the processor 118 executing instructions 136 stored in the memory 120 (FIG. 1). Additionally, the particular sequence of steps shown in the procedure 900 of FIG. 9 is provided by way of example and not limitation. Thus, the steps of the procedure 900 may be executed in sequences other than the sequence shown in FIG. 9 without departing from the scope of the present disclosure. Further, some steps shown in the procedure 900 of FIG. 9 may be concurrently executed with respect to one another instead of sequentially executed with respect to one another.

During head-tracking, the user's head pose is continually updated at block 902. In particular, the x-, y-, z-orientation and roll, pitch, and yaw of the user's head is tracked and updated. As part of the updating, translational velocity is calculated from the user's head pose at block 904. The translational velocity indicates how quickly the user head movements are being made side to side, up or down, and in and out, relative to a fixed location (for example, on display 122) a predetermined distance away from the user. Concurrently with the performance of the operation at block 904, the YZ velocity of orientation (for example, the nodding motion of the user's head) is calculated from the user's head pose at block 906, and roll is extracted from the user's head pose at block 908. At block 910, the x-coordinate from the calculated translational velocity determined at block 904 is isolated. The x-coordinate indicates a movement of the user's head toward or away from the fixed location (for example, the display 122). The x-coordinate is mapped at block 912, an example of which is provided in FIG. 10A. The map is a quadratic mapping of the velocity of the user's head on the x-axis and the velocity of the patient image capture device 109 on the y-axis. As illustrated in FIG. 10A, the quadratic map shows an inverse proportionality between the velocity of the user's head and the velocity of the patient image capture device 109 until a predetermined velocity of each is reached, where the relationship between the two indicates no movement of the patient image capture device 109 despite the increase in the velocity of the user's head. It will be appreciated that the map may illustrate a different relationship between the two velocities, in other embodiments. For example, rather than quadratic mapping, the relationship may be mapped as a linear, non-linear, or other function.

Returning to block 904, the z-coordinate from the calculated translational velocity determined at block 914 is mapped at block 916. In addition, the YZ velocity of orientation from block 906 is quadratically mapped at 918. In other embodiments, rather than quadratic mapping, the relationship may be mapped as a linear, non-linear, or other function. Next, the results from blocks 916 and 918 are combined to yield a pan angular velocity. Additionally, the roll extracted at block 908 is mapped at block 920 to yield a roll angular velocity, an example of which is provided in FIG. 10B. Similar to the map in FIG. 10A, the map in FIG. 10B includes the velocity of the user's head on the x-axis and the velocity of the patient image capture device 109 on the y-axis. However, here, the image capture device 109 movement is restricted to a range of velocities of head movement. Returning to FIG. 9, at block 922, an integral of the in/out velocity, pan angular velocity, and the roll angular velocity is calculated to determine a pose of the image capture device 109. Once determined, corresponding signals are provided to the image capture device 109 or corresponding arm 106 to move the image capture device 109 to the appropriate position. In an embodiment, prior to being provided to the image capture device 109 and/or the robotic arm 106, filtering or smoothing operations may be applied to data points making up the output from block 922, for example, by curve fitting, using digital filters, low-pass filters, exponential smoothing, and the like, to remove noise or other unwanted data points. As a result, a modified corresponding signal is output to thereby move the robotic arm 106 or the image capture device 109 in a relatively smooth motion.

Figure 11:
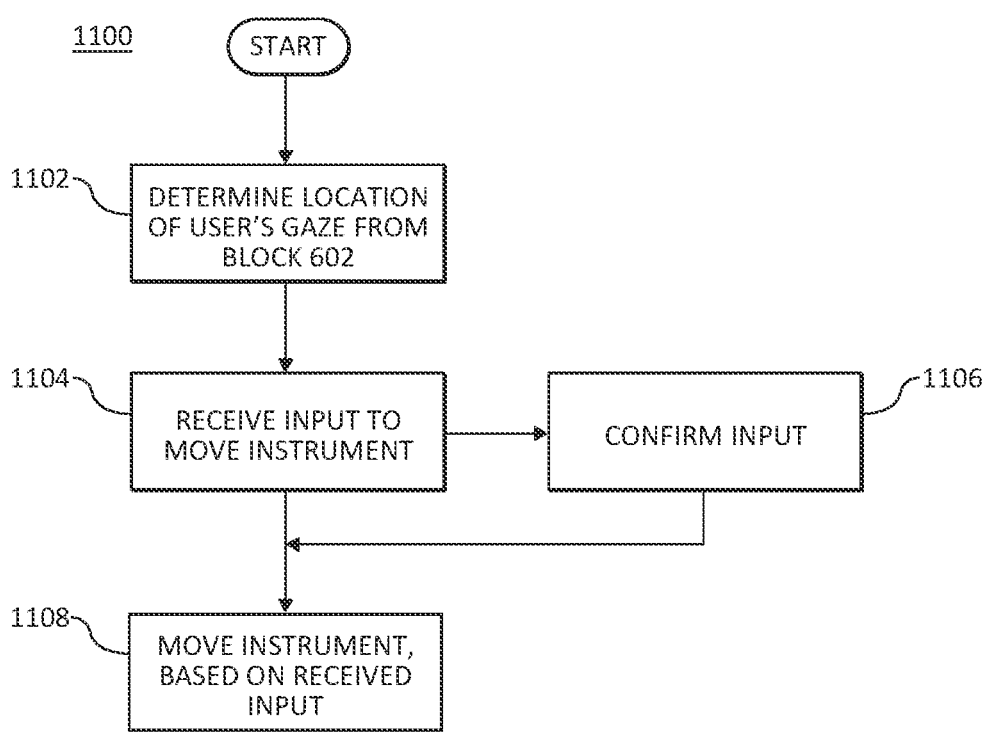
FIG. 11 a flow diagram of a method for controlling a robotic surgical system, in accordance with still yet another aspect of the present disclosure.

FIG. 11 is an exemplary computer-implemented procedure 1100 for controlling the robotic arm 106, and in particular, movement of the instrument 108 coupled to the robotic arm 106, based on the relationship between the identified user location and the surgical site image described in block 612 of procedure 600, accordance with still another embodiment. The procedure 800 may be implemented, at least in part, by the processor 118 executing instructions 136 stored in the memory 120 (FIG. 1). Additionally, the particular sequence of steps shown in the procedure 1100 of FIG. 11 is provided by way of example and not limitation. Thus, the steps of the procedure 1100 may be executed in sequences other than the sequence shown in FIG. 11 without departing from the scope of the present disclosure. Further, some steps shown in the procedure 1100 of FIG. 11 may be concurrently executed with respect to one another instead of sequentially executed with respect to one another.

The procedure 1100 includes determining a location of the user, for example from block 602 of procedure 600, based on the captured image of the user using any one of various algorithms suitable for calculating a location of the user's eye gaze from the captured image of the user, at block 1102. The location of the user may be determined from eye-tracking or head-tracking algorithms for calculating the location of the eyes or head of the user. An input to move the instrument is received at block 1104. The input may be received from the input device 138, for example, by the user depressing a button, providing input to a mouse, or selecting an icon on a touchscreen. Alternatively, the input may be detected from the captured images of the user. For example, the images captured by the image capture device 128 directed at the user captures still images and/or video of the user's eyelid movements, which may include double blinks, sustained closing of the eyes, winks or another eye movement. The eye movements each may be associated with commands to move the instrument 108 in a desired manner, such as opening or closing grasper jaws, turning tools on or off, and the like. In another embodiment, the images captured by the image capture device 128 directed at the user captures still images and/or video of the user's head movements, which may include nodding, head shaking, moving the head from side to side, or other head movements. Each head movement likewise, may be associated with a different command to move the instrument in a particular manner.

In an embodiment, the user's input is confirmed at block 1106. To confirm that the input detected from the captured images of the user is an intended gesture, the determination of the user's location includes determining whether the user's location is held for a time that is greater than a threshold amount of time, such as one (1) second or more. In embodiments in which the input is provided via user movements detected from the images captured by the image capture device 128, confirmation of the input may effected for example, by the user depressing a button, providing input to a mouse, or selecting an icon on a touchscreen.

In response to the received input, the system 10 moves the instrument in the desired manner at block 1108. Thus, as noted above, instrument movement associated with the particular gesture, for example, blinking to indicate opening or closing grasper jaws, nodding to indicate turning tools on or off, and the like, is performed.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)." The term "clinician" may refer to a clinician or any medical professional, such as a doctor, nurse, technician, medical assistant, or the like, performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A system for robotic surgical device control, comprising:
   a robotic arm coupled to a patient image capture device;
   an autostereoscopic display configured to display an image of a surgical site obtained from the patient image capture device;
   a user image capture device;
   an image processor configured to identify a location of at least part of a user in an image obtained from the user image capture device; and
   a controller configured to:
      in a first mode, adjust a three dimensional aspect of the image displayed on the autostereoscopic display based on the identified location, and, in a second mode, move the robotic arm based on a relationship between the identified location and the surgical site image;
      detect a change of a location of an eye gaze of a user relative to the autostereoscopic display;
      cause the system to move the robotic arm coupled to the patient image capture device based on the detected change of location of the eye gaze;
      determine whether the detected change of location of the eye gaze is outside of a first predetermined range of distances from a predetermined location;
      determine whether the detected change of location of the eye gaze is outside of a second predetermined range of distances that is greater than the first predetermined range of distances; and
      cause the system to provide a notification to the user in response to the determination of the detected change of location of the eye gaze being outside of the second predetermined range of distances, wherein the second predetermined range of distances includes distances that are outside of an outer perimeter of the image of the surgical site displayed on the autostereoscopic display, and wherein the notification includes an audible or visual indication that the eye gaze of the user is outside of the outer perimeter of the image of the surgical site displayed on the autostereoscopic display.

2. The system of claim 1, wherein:
   the autostereoscopic display is further configured to include a plurality of pixels including even pixel columns and odd pixel columns;
   each pixel column is disposed below a corresponding vertical lens;
   the vertical lenses corresponding to the even pixel columns are configured to permit the even pixel columns to be perceptible by a first eye of the user; and
   the vertical lenses corresponding to the odd pixel columns are configured to permit the odd pixel columns to be perceptible by a second eye of the user.

3. The system of claim 2, wherein the controller is further configured to adjust the image displayed on the autostereoscopic display for improved perception by the user by adjusting one or more of the pixels of the plurality of pixels.

4. The system of claim 3, wherein:
   the image processor is further configured to identify the locations of the first eye and the second eye of the user in the image obtained from the user image capture device; and
   the controller is further configured to adjust the one or more pixels of the plurality of pixels displayed on the autostereoscopic display based, in part, on the identified location of the first eye of the user or the identified location of the second eye of the user.

5. The system of claim 1, wherein the patient image capture device is configured to achieve a first predetermined latency in capturing and transmitting to the image processor visual content, and the image processor comprises multiple sub-processors in parallel execution to achieve a second predetermined latency in processing the visual content, determining the location of the eye gaze of the user, and transmitting a control signal to the patient image capture device.

6. The system of claim 1, wherein the controller is further configured to, in response to the detected change of the location of the eye gaze of the user, calculate a velocity magnitude and direction at which to move the arm.

7. The system of claim 1, wherein the controller is further configured to determine whether the eye gaze of the user is held at the location for a time period that is greater than a threshold time period, and in response to the eye gaze being held for the time period greater than the threshold time period, move the robotic arm coupled to the patient image capture device.

8. The system of claim 1, wherein the controller is further configured to:
   detect an input to move the patient image capture device;
   determine a change in the identified location;
   determine a head position and/or velocity, based on the change in the identified location; and
   determine one or more of a head tilt, a head orientation, or a head roll, based on the determined head position and/or velocity.

9. The system of claim 1, wherein the controller is further configured to:
   determine a head pose, based on the identified location;
   calculate a translational velocity based on the determined head pose;
   map an x-coordinate from the calculated translational velocity to yield an in/out velocity;
   map a z-coordinate from the calculated translational velocity, calculate an YZ velocity of orientation based on the determined head pose, and map the calculated YZ velocity to yield a pan angular velocity;
   extract roll values from the determined head pose;
   map the extracted roll values to yield a roll angular velocity; and determine a pose of the patient image capture device, based on the in/out velocity, the pan angular velocity, and the roll angular velocity.

10. The system of claim 1, wherein the robotic arm includes an endoscope.

11. The system of claim 1, wherein the controller is configured to perform in both the first mode and the second mode concurrently.

12. The system of claim 1, wherein the controller is configured to perform in the first mode and the second mode separately.

13. The system of claim 1, wherein the notification includes an arrow displayed on the autostereoscopic display, the controller being further configured to adjust a length of the displayed arrow in proportion to an amount the location of the eye gaze of the user is outside of the second predetermined range of distances.

14. The system of claim 1, wherein the autostereoscopic display includes:
a screen having a first set of pixels and a second set of pixels; and
a lenticular lens layer disposed in front of the screen and having a plurality of first vertical lenses disposed over the corresponding first set of pixels and configured to be directed at an angle suitable to permit visual content of the first set of pixels to be perceived by a first eye of the user, and a plurality of second vertical lenses disposed over the corresponding second set of pixels and configured to be directed at an angle suitable to permit visual content of the second set of pixels to be perceived by a second eye of the user.

15. The system of claim 1, wherein the image capture device is fixed to the autostereoscopic display.

16. The system of claim 1, wherein the controller is configured to cause the system to provide the notification to the user in response to the determination of the detected change of location of the eye gaze being outside of the second predetermined range of distances for longer than a threshold period of time.

* * * * *